Figure 1:
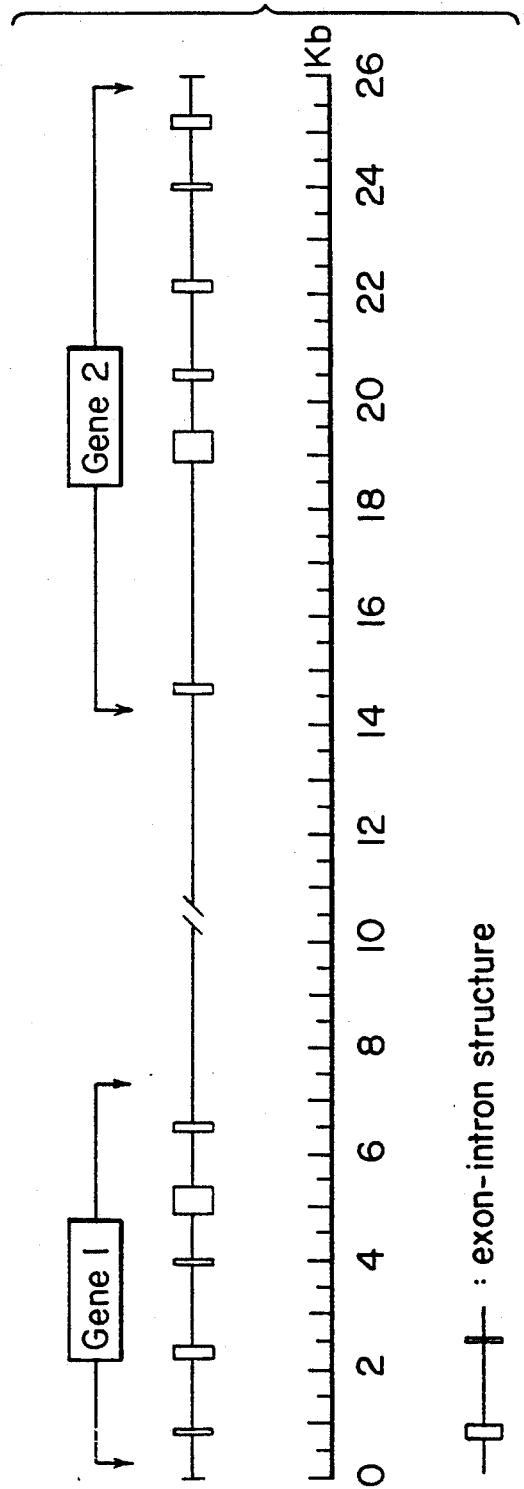

United States Patent [19]

Reth

[11] Patent Number: 5,252,475
[45] Date of Patent: Oct. 12, 1993

[54] METHODS AND VECTORS FOR SELECTIVELY CLONING EXONS

[75] Inventor: Michael Reth, Freiburg, Fed. Rep. of Germany

[73] Assignee: Max-Planck-Gesellschaft zur Forderung der Wissenschaften e.V., Gottingen, Fed. Rep. of Germany

[21] Appl. No.: 725,608

[22] Filed: Jul. 3, 1991

[30] Foreign Application Priority Data

Jul. 5, 1990 [DE] Fed. Rep. of Germany ....... 4021458

[51] Int. Cl.$^5$ ...................... C12N 15/10; C12N 15/85; C12N 5/10; C07H 21/04
[52] U.S. Cl. ............................... 435/172.3; 435/320.1; 435/240.2; 536/23.1
[58] Field of Search ............... 435/240.2, 172.1, 172.3, 435/320.1

[56] References Cited
FOREIGN PATENT DOCUMENTS 0201184 12/1986 European Pat. Off. .

OTHER PUBLICATIONS

Cullen, Cell, vol. 46, 973–982 (1986).
Auch et al. (Dec. 1990), Nucl. Acids Res., vol. 18 (22), pp. 6743–6744.
Cepko et al. (Jul. 1984), Cell, vol. 37, pp. 1053–1062.

Primary Examiner—Richard A. Schwartz
Assistant Examiner—Philip W. Carter
Attorney, Agent, or Firm—Birch, Stewart, Kolasch & Birch

[57] ABSTRACT

The invention relates to a method for selectively cloning exons in which an eukaryotic genomic DNA fragment to be assayed is cloned into a shuttle vector in a cloning site of an intron flanked by exons. Upon expression in eukaryotic cells, exons present in the cloned DNA are spliced to the exons flanking the intron. After amplification of the cDNA of the expressed mRNA with primers specific for the exons in the vector by PCR, selectively cloned exons can be detected due to the size of the PCR product. The invention also relates to vectors used to carry out the method of the invention as well as to exon libraries.

26 Claims, 6 Drawing Sheets

METHODS AND VECTORS FOR SELECTIVELY CLONING EXONS

The invention relates to methods for selectively cloning exons and for producing exon libraries. The invention also relates to exon libraries produced by using these methods. In addition, the invention relates to vectors for selectively cloning exons and to host organisms containing the described vectors in which exons have been selectively cloned.

In eukaryotic genomes the products of most genes are not encoded by a continuous DNA region. Rather, these products usually comprise a plurality of exons separated from each other by introns. These exons are 10 to several 100 base pairs (bp) long. It is only after transcription of a gene that the mRNA sequences corresponding to the exon sequences become attached to each other by a splicing mechanism, resulting in mature mRNA. The predominant portion of the eukaryotic genome is non-coding DNA. This is, for example, due to the fact that introns generally are much greater in size than exons (usually from 100 bp to 300 kilo base (kb)) and the fact that adjacent genes may be separated from one another by large portions of non-coding DNA of about 2 to 200 kb.

During the last 10 to 20 years, molecular biology has developed a number of methods which facilitate analysis of eukaryotic genomes and individual genes. It is possible to clone genomic DNA fragments of various sizes (0.1 to 300 kb) by means of lambda phages, cosmid or YAC vectors. Total RNA, poly(A) RNA, or specific mRNA can be transcribed into cDNA by reverse transcriptase and then cloned. Specific sequences can be propagated and cloned by the PCR technique.

However, all of these cloning methods require a specific probe, i.e., a DNA fragment containing the specific sequences of the gene to be detected. So far, it has only been possible to obtain such a probe with considerable efforts either via the protein sequence of a known gene product or by means of subtracting cDNA libraries. Hence, it has not been possible to date to clone large numbers of genes of the eukaryotic genome that have been defined only genetically. Even if a larger region (10 to 200 kb) of a potential gene locus has been cloned, it is very difficult to find a gene therein. The cloned region must first be mapped. Then subfragments must be isolated from that region. From the subfragments probes are produced and assayed for potential expression in the Northern blot. A lot of these probes are located in the intron region. Since the introns of the eukaryotic genome are full of repetitive sequences and since a lot of these repetitive sequences are transcribed, this method gives a large number of false results and a gene can only be found by laborious analysis using a lot of probes.

Therefore, the technical object underlying the invention is to provide methods for selectively isolating exon sequences from large genomic DNA fragments by cloning. It is a further technical object of the invention to provide vectors useful in carrying out these selective cloning methods.

This technical object can be achieved by providing the embodiments characterized in the patent claims.

Thus the invention relates to a method (exon trap method) for selectively cloning exons comprising the following steps:

(a) cloning a genomic DNA fragment to be assayed for exons into a cloning site of a vector having the following features:
  (aa) it is a shuttle vector for prokaryotic and eukaryotic host cells which may contain selective marker genes,
  (ab) it contains a DNA fragment comprising the following elements arranged in the 5'-3' direction:
    a eukaryotic promoter,
    a 5' exon of a gene, and
    at least the 3'-terminal exon of a gene, said arrangement of elements permitting the synthesis of a functional transcript, with a cloning site being located in an intron following the 5' exon,
  thereby constructing a recombinant vector;
(b) transfecting eukaryotic host cells with the recombinant vector;
(c) expressing the recombinant vector in the transfected host cells;
(d) isolating total RNA, preferably poly(A) RNA, from the host cells in (c);
(e) producing cDNA with the RNA indicated in (d), using a primer for the synthesis with reverse transcriptase, which primer is complementary to a region of an exon located downstream from the cloning site;
(f) carrying out a PCR reaction with the cDNA indicated in (e) and a primer pair, the first primer being complementary to a region of the exon located upstream from the cloning site and the second primer being complementary to a region of an exon located downstream from the cloning site;
(g) cloning in a vector the DNA fragment containing the additional exon(s) and obtained in the PCR reaction in (f).

The term "shuttle vector" refers to a vector capable of replicating in different host species. The shuttle vector used in the method of the invention has one origin each for replication in prokaryotic and eukaryotic cells.

The term "5' exon of a gene" refers to an exon of a gene carrying a donor splice site. The term "3'-terminal exon of a gene" refers to a terminal exon of a gene carrying an acceptor splice site. The vector to be used in step (A) preferably contains only two exons between which the genomic DNA fragment to be analyzed is cloned.

The invention further relates to a method to produce an exon library by inserting a number of genomic DNA fragments into the mentioned cloning vectors and by carrying out the following step in addition to the steps of the above-discussed method:

(h) transforming or transfecting host cells for an exon library with the recombinant vectors obtained in (g).

It is preferred to use bacterial host cells, e.g., *E. coli*.

In a preferred embodiment of the method of the invention either primer used in the PCR reaction in (f) carries at its 5' end the recognition sequence of a desired restriction endonuclease. This facilitates subsequent cloning in a vector having a cloning site which is recognized by the same restriction enzyme. Exons can only be cloned by the method of the invention if the genomic fragments to be tested have been integrated into the vector with the right orientation in respect to the transcriptional direction of the gene containing the exon.

In a particularly preferred embodiment of the method of the invention DNA fragments larger than the DNA fragment obtained only by the vector in the PCR reaction are isolated, e.g., by gel electrophoresis, prior to cloning the DNA fragments in step (g) obtained by the PCR reaction. This step excludes all those PCR products from subsequent cloning in which only vector DNA has been amplified. This step is particularly advantageous in the production of exon libraries because the background of PCR products containing no newly cloned exons is reduced.

In a preferred embodiment of the method of the invention the recombinant vectors are propagated by cloning in a suitable host cell, preferably in *E. coli*, prior to steps (b) and/or (h).

In another preferred embodiment of the method of the invention the eukaryotic promoter is a strong promoter, preferably LTR (Long Terminal Repeat) of RSV (Rous Sarcoma Virus).

In a particularly preferred embodiment of the invention the 5' and 3' exons contained in the vector indicated in feature (ab) have been derived from a rat insulin gene.

In a further preferred embodiment of the method of the invention the genomic DNA fragments are isolated from a chromosomal region to be analyzed. The desired chromosomal regions are excised from the chromosome and inserted into the vectors by microcloning techniques. According to the invention, genes allocated to particular chromosomal regions by genetic mapping can be cloned rapidly and as desired.

In a further preferred embodiment of the method of the invention the genomic DNA fragments are derived from a genomic gene library.

In addition, the invention relates to an exon library produced by the method of the invention.

The invention further relates to a vector (exon trap) comprising the following features:
(a) it is a shuttle vector for prokaryotic and eukaryotic host cells which may contain selective marker genes;
(b) it contains a DNA fragment comprising the following elements arranged in the 5'-3' direction:
  a eukaryotic promoter,
  a 5'-exon of a gene, and
  at least the 3'-terminal exon of a gene, said arrangement of elements permitting the synthesis of a functional transcript, with a polylinker being located in an intron following the 5' exon.

The terms used in this context are defined as above. The vector can be used as a tool to carry out the method of the invention. Therefore, the invention also relates to the mentioned vector comprising a genomic DNA fragment inserted into the polylinker.

In a preferred embodiment the vector contains a eukaryotic promoter which is a strong promoter. In a particularly preferred embodiment the promoter is LTR of RSV.

In a further particularly preferred embodiment the 5' and 3' exons integrated into the vector and indicated in (b) are derived from rat insulin gene.

A particularly preferred embodiment of the recombinant vector contains a genomic DNA fragment from a genomic gene library.

In a further particularly preferred embodiment of the recombinant vector the genomic DNA fragment is derived from a chromosomal region to be analyzed.

The invention also relates to host organism transfected or transformed with the vector of the invention. These host organisms may be prokaryotic or eukaryotic host organisms within which the vector can be replicated.

The figures show:

FIG. 1: a gene organization of the eukaryotic genome. Most of the eukaryotic genes are not coded by a continuous DNA sequence. Rather, the sequence information of a gene is distributed to a plurality of exons. These exons are separated from each other by intron sequences and are joined only in the RNA read by the gene (exon splicing). In this regard, intron sequences are generally much larger than exon sequences. What is more, two adjacent genes are separated from one another by a larger region of the non-coding DNA sequence.

Figure 2:
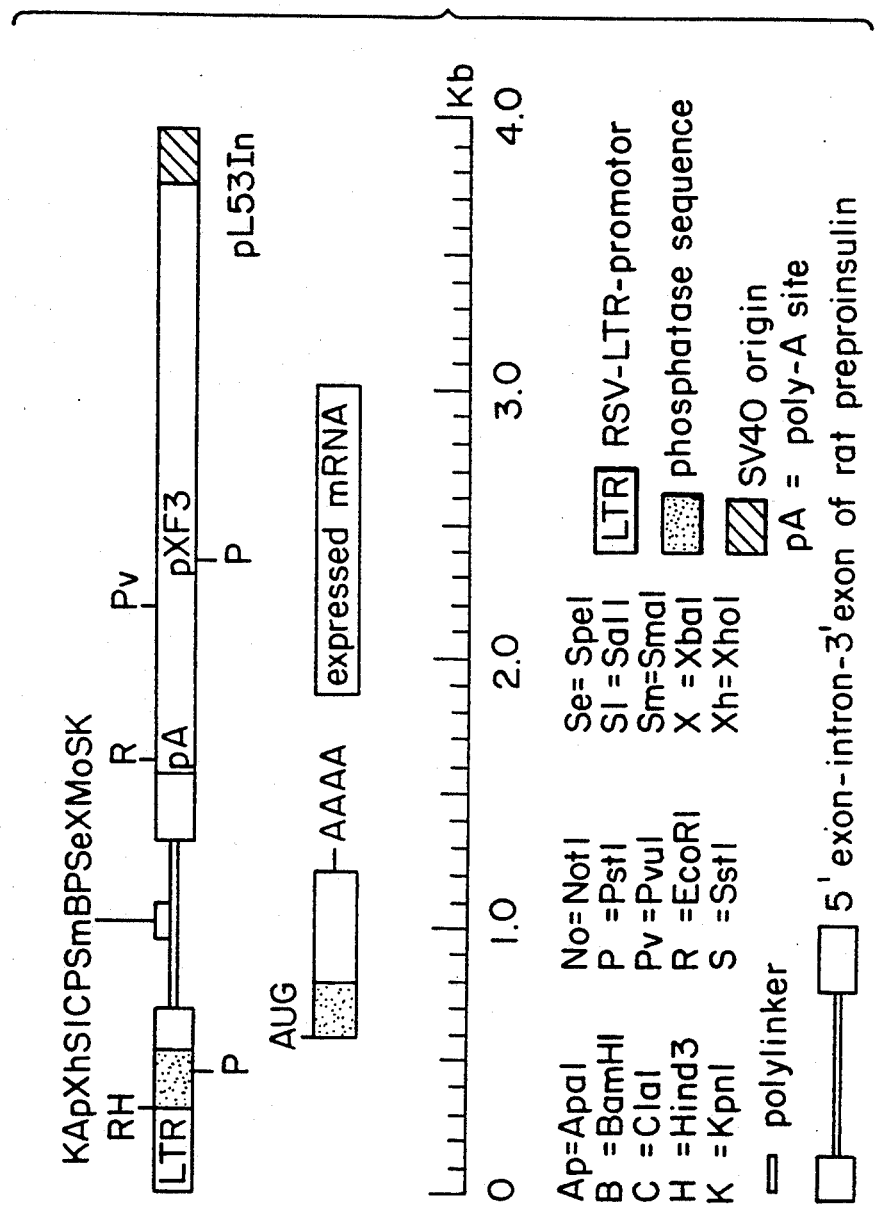

FIG. 2: the restriction map of vector pL53In for selectively cloning exons. The vector contains the LTR promoter of the Rous Sarcoma Virus (RSV), the 5' region of a phosphatase gene with the ATG start codon and part of the second and third exons of the rat preproinsulin gene. These sequences have been cloned into plasmid pXF3 which also carries the replication initiation site of the SV40 virus. The vector can be transiently expressed in eukaryotic cells and produces therein mRNA containing phosphatase and insulin sequences.

Figure 3:
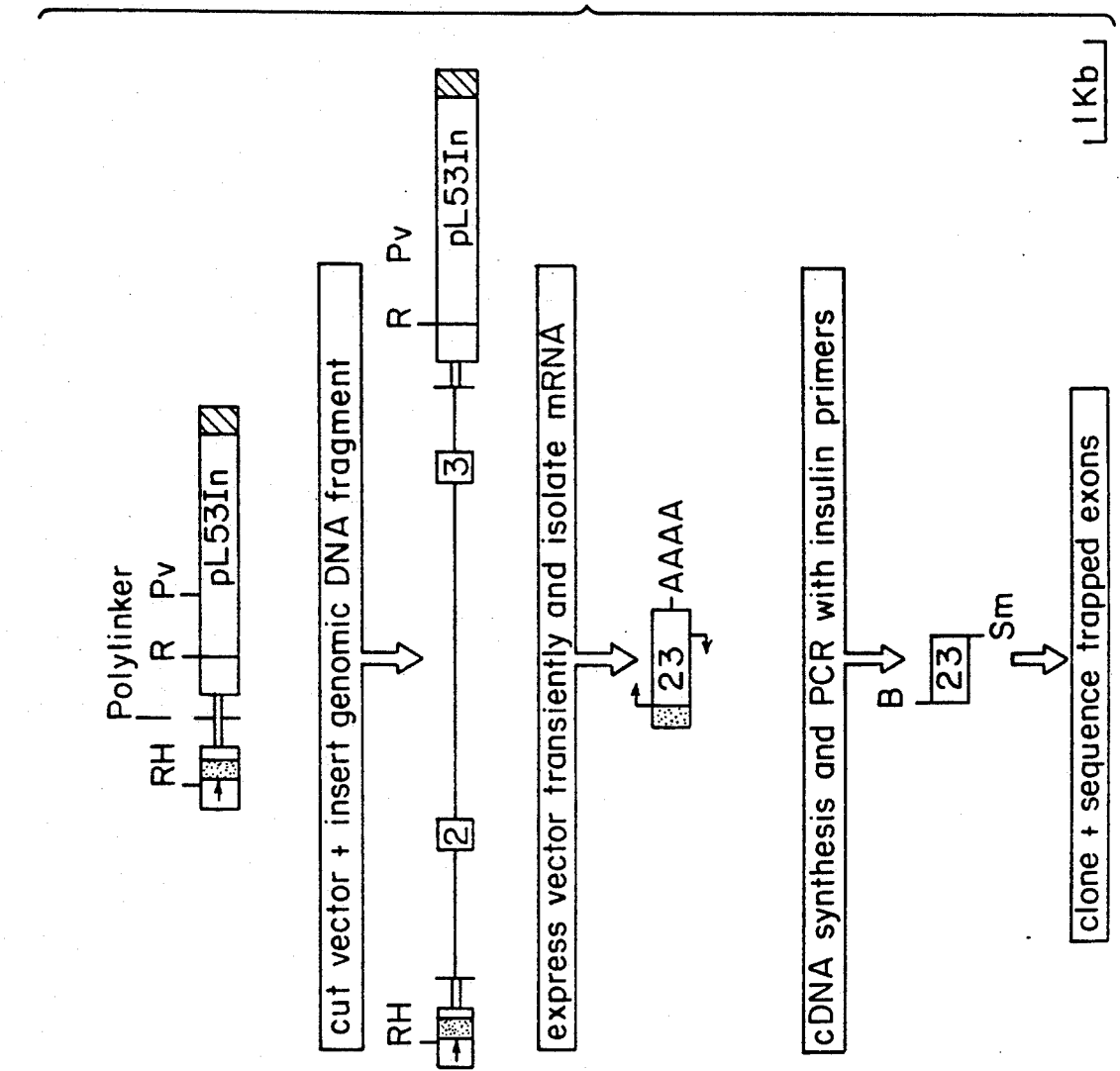

FIG. 3: exon cloning methods. The vector for selectively cloning exons was linearized with a restriction enzyme in the polylinker in the intron and a genomic DNA fragment was inserted into the restriction site. The recombinant vector was "transiently" expressed in eukaryotic cells (e.g., COS cells) for 2 days. Then mRNA was isolated from these cells. Based on the RNA containing insulin sequences, cDNA was produced using a specific primer and the reverse transcriptase enzyme. The specific cDNA was then propagated with a 5', 3' insulin primer pair by means of PCR and cloned into a vector for further analysis.

Figure 4:
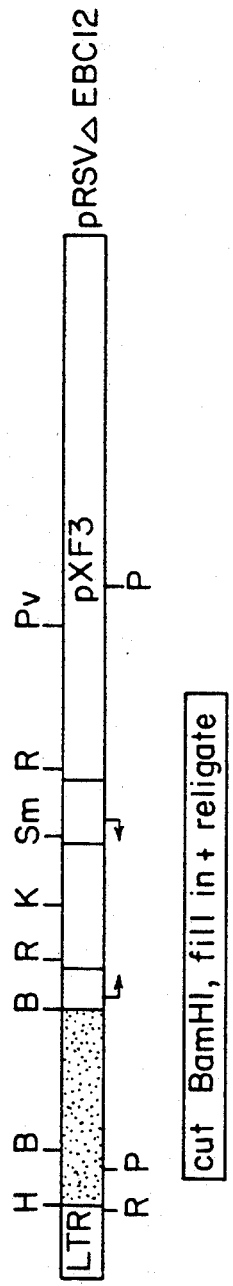
Figure 4:
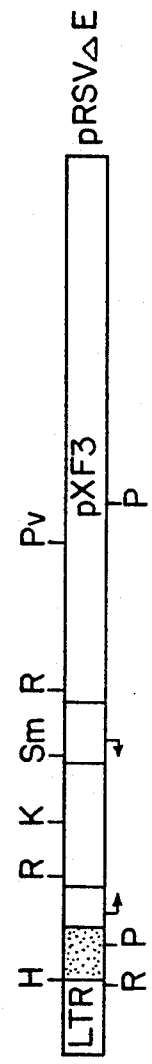
Figure 4:
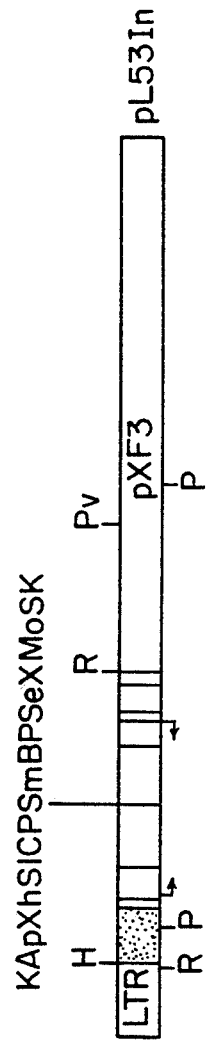
Figure 4:
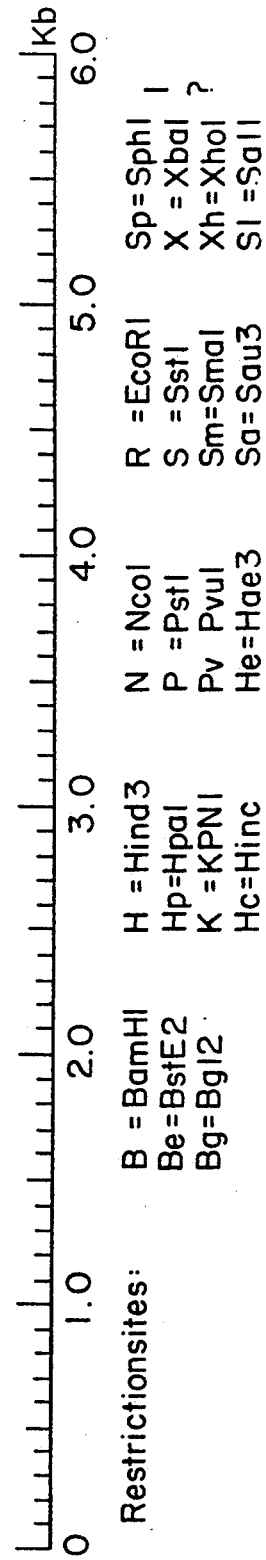

FIG. 4: the construction of vector pL53In for selectively cloning exons. All cloning steps (restriction cleavage, ligation, transformation) were carried out according to standard protocols (see Sambrook et al., "Molecular Cloning", 2nd revised edition, Cold Spring Harbor, 1989).

Figure 5:
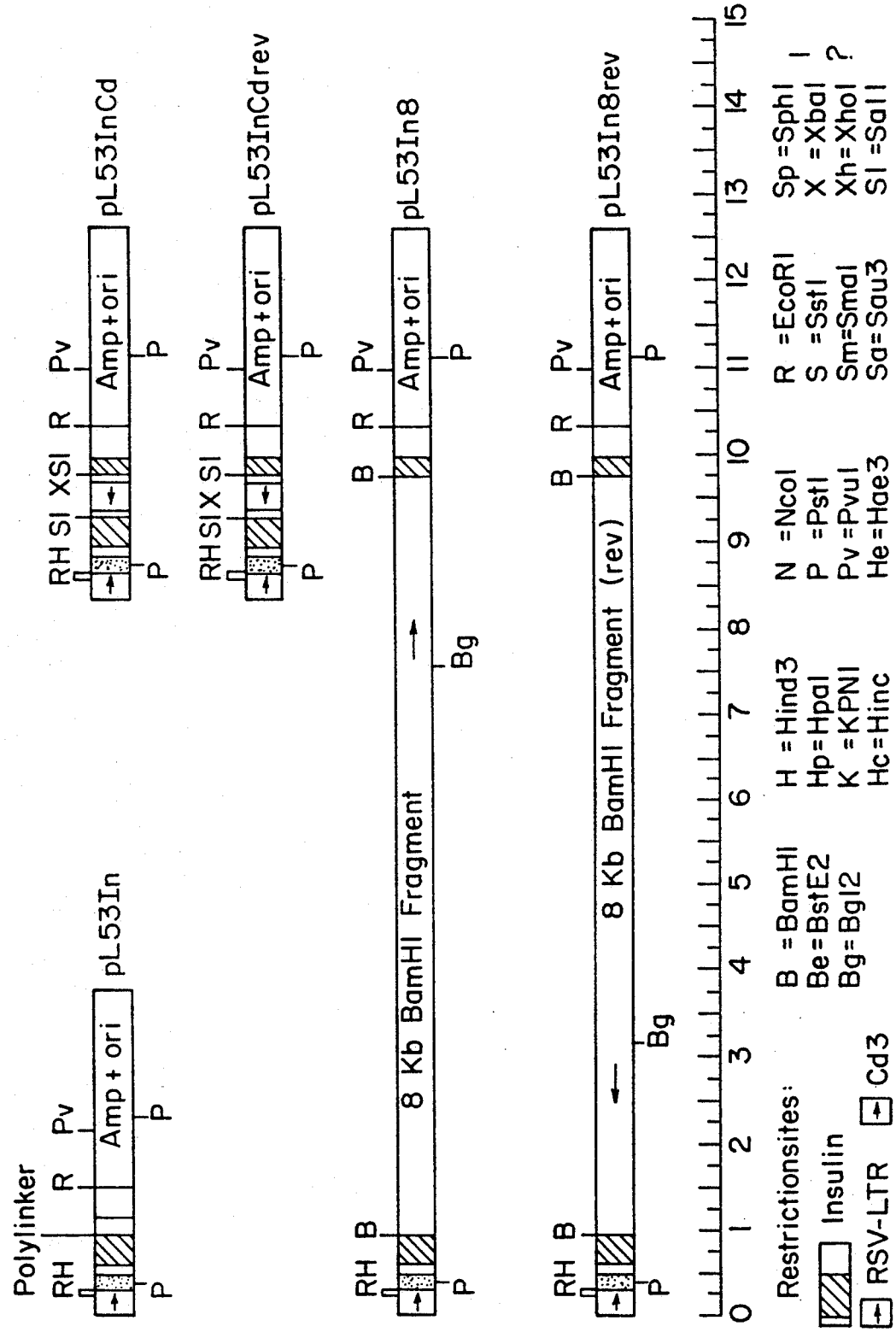

FIG. 5: the construction of the recombinant pL53In vectors pL53InCδ and pL53In8.

Figure 6:
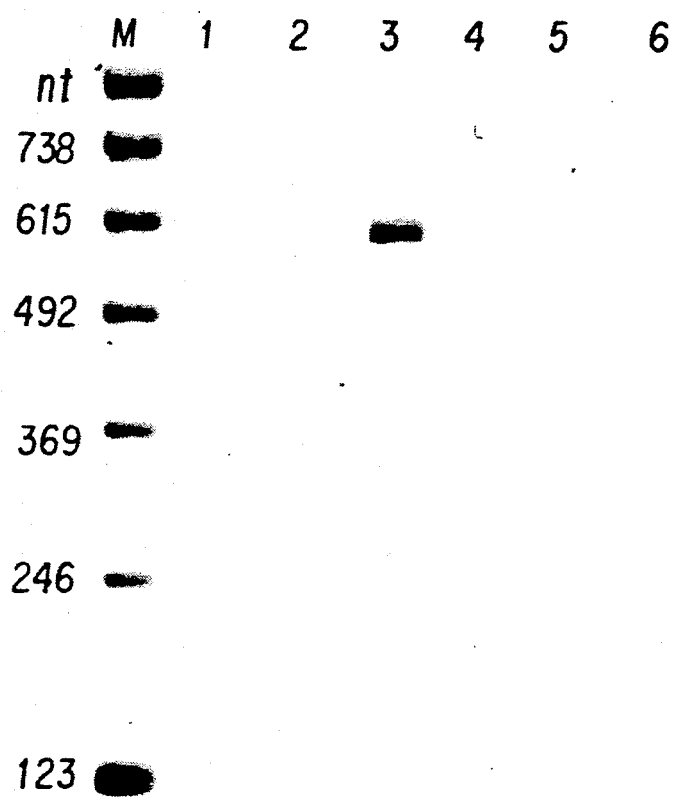

FIG. 6: the analysis of the PCR fragments on agarose gel. One fourth of the amount of fragments obtained by the PCR method was placed on a 1% agarose gel and analyzed. The gel was dyed with ethidium bromide to detect DNA and is shown as a negative. PCR was carried out with insulin-specific cDNA from COS cells transfected with the following vectors: cloning vector pL53In (lane 2), recombinant vectors pL53InCδ (lane 3), pL53InCδrev (lane 4), pL53In8 (lane 5) and pL53In8rev (lane 6). Lane 1 shows the PCR product applied as a control after cDNA synthesis of COS cells transfected with pUC19. Lane M contains a size marker. Vectors pL53InCδ and pL53InCδrev contain 600 bp of large genomic DNA fragments having the mouse Ig C-delta 3 exon both in the right and the wrong orientations. Only the right orientation (in pL53Incδ) gives a PCR fragment which corresponds in size (600 bp) exactly to the insulin fragment (250 bp) plus the trapped C-delta 3 exon (340 bp). Vectors pL53In8 and pL53In8rev each contain a genomic 8 kb long DNA fragment having an unknown sequence and cloned in both orientations. Only in one orientation was an exon of 160 bp trapped between the two insulin exons. This shows that the exon trap method of the invention enables small exons to be isolated specifically from large genomic DNA fragments.

The method for selectively cloning exons (exon trap method) of the invention makes it much easier to analyze potential gene loci. A large DNA region can be assayed for exons without prior mapping, by cloning DNA fragments of this region in vectors of the invention, e.g., in vector pL53In. The method for selectively cloning exons makes it possible to identify gene carrying DNA fragments very quickly. These are all fragments from which "trapped" exons can be obtained. With this method an exon and thus a part of the desired gene can be cloned directly and it is easy to obtain from the cloned exon a specific probe with which the entire gene can then be cloned.

Consequently, work that usually takes months or years can be achieved in weeks by using the method of the invention. Therefore, it is particularly useful in genome projects, for example, when analyzing human genomes.

The restriction map of shuttle vector pL53In of the invention is depicted in FIG. 2. pL53In is a derivative of plasmid pBC12/RSV/SEAP (Cullen, Cell 46 (1986), 973-982). It contains LTR of RSV as the strong promoter, followed by a short region of a phosphatase gene sequence and the 3' portion of the rat preproinsulin gene. The genomic insulin gene sequence includes a part of the second exon with the 5' donor splice site, a shortened intron of 600 bp and the complete last insulin exon with the 3' acceptor splice site and a 3' polyadenylation site. A polylinker was inserted into the insulin intron to make cloning easier. This DNA sequence was cloned into the pBR322 derivative pXF3 carrying the gene for ampicillin resistance and the prokaryotic origin of replication. The resulting vector pL53In also includes 200 bp of the SV40 replication origin. This leads to the vector being replicated in eukaryotic cells as long as these express the large T antigen. After transfection in eukaryotic cells, pL53In expresses a poly(A)+ RNA with an AUG start codon in the phosphatase sequence and the two spliced insulin exons; see FIG. 2. If a genomic DNA fragment containing an exon is cloned in the right orientation into the polylinker site of the insulin intron, the vector will express RNA within which the inserted exon is spliced together with the two insulin exons.

To assay a large genomic DNA fragment for the presence of exon sequences by means of the method of the invention, this fragment was cloned in both orientations into the polylinker of pL53In (FIG. 3). The two recombinant vectors were then expressed transiently in COS cells. After 2 days total RNA was isolated from transfected cells. Insulin coding cDNA was produced by using a specific oligomer primer complementary to a sequence in the 3' insulin exon. The cDNA thus obtained was then amplified by PCR using a primer pair complementary to a region in the 5' or 3' insulin exon. If necessary, the PCR reaction can be repeated with a different primer pair. The amplified DNA was then analyzed on a 1% agarose gel. After amplification by the PCR technique, an exon additionally integrated into the vector can be visualized due to its differing size compared to the amplified vector sequence. The PCR method described in the present invention has been described in detail, e.g., in EP-A2 201 184.

The examples illustrate the invention. Further details on the methods of molecular biology as used herein can be taken from "Molecular Cloning", supra.

EXAMPLE 1

Construction of vector pL53In for selectively cloning exons.

The starting plasmid for the construction of pL53In was pRSVΔEBC12 (FIG. 4). A gene on that plasmid codes for a phosphatase. The plasmid had been used to date to analyze promoter enhancer constructions. The strength of a promoter was measured in terms of the amount of phosphatase secreted. The two insulin exons having an intron in between had only been inserted into the plasmid for better expression of the RNA phosphatase. Plasmid pRSVΔEBC12 was cleaved with BamHI, the restriction site filled up with polymerase and the plasmid religated. Thus the BamHI restriction sites and most part of the phosphatase gene were deleted (pRSVΔE). Subsequently, the EcoRI restriction site in the intron and the SmaI restriction site in the 3' insulin exon were deleted. A polylinker (similar to that in the bluescript vector) was inserted into the KpnI restriction site. This cleavage yielded the finished vector pL53In (see FIG. 4).

EXAMPLE 2

Construction of recombinant pL53In vectors.

To assay the method for selectively cloning exons, recombinant pL53In vectors were constructed with DNA fragments cloned into the polylinker in the intron (FIG. 5). The first two vectors contained a 600 bp SalI fragment carrying the exon (cδ3) of the Ig delta gene. This fragment was cloned in both orientations into the SalI restriction site of the polylinker in the intron. The resulting plasmids were called pL53INCδ and pL53INCδrev. Only pL53INC carried the C-delta 3 exon in the right direction so as to allow that it be inserted (spliced) into RNA with the two insulin exons. To construct pL53In8 and pL53In8rev, an 8 kb long genomic BamHI fragment of a potential gene locus was cloned in both orientations into the BamHI restriction site of the polylinker.

EXAMPLE 3

Transfection of eukaryotic cells (COS) with recombinant pL53In DNA.

The COS-7 cells required for transfection grew adherently so to reach a density of $10^6$ cells per culture plate (9 cm plates with 10 ml of medium). The culture medium was RPMI admixed with 10% FCS (fetal calf serum). To harvest the COS cells, the medium was sucked off and the plates washed once with 10 ml of sterile PBS (37° C.). 1 ml of a trypsine/EDTA solution (0.5 g trpysine; 0.2 g EDTA; 0.85 NaCl/liter) was then added to each plate. After incubation for 5 to 10 minutes at room temperature (RT), the cells became detached from the plate. The cells from one plate were then added to 10 ml of RPMI+5mM HEPES (pH 7.4, 37° C.) buffer. The buffer was transferred from one plate to the other until all cells had been harvested, and then poured into a 50 ml tube. The above process was repeated once again with 10 ml of RPMI/HEPES buffer and the 50 ml tube filled up with 30 ml of RPMI/HEPES buffer. The cells were separated by centrifugation at 1,500 rpm at RT. The cell precipitate was added to 10 ml of Tris saline buffer, pH 7.4 (8 g NaCl; 0.38 g KCl; 0.025M Tris, pH 7.4, per liter). The cells were counted and the cell suspension comprising the Tris saline buffer adjusted to a cell density of $10^6$ per ml. All buffers used had been preheated to 37° C. In each case 1 ml of cell suspension ($10^6$ cells) was poured into a 15 ml tube and maintained at 37° C. until the transfection mixture was added.

Circular recombinant pL53In DNA was mixed with TE buffer (pH 7.4) to give a concentration of 100 ng/μl. To produce the transfection mixture, 50 μl (5 μg) of DNA solution was poured into an Eppendorf tube, mixed with 500 μl of transfection buffer (Vortex) and incubated for one hour at 37° C.
10 ml of transfection buffer:
6.6 ml of RPMI
3.2 ml of 50 mM Tris, pH 7.4
0.25 ml of DEAE dextran, 10 mg/ml in $H_2O$.
The DEAE dextran solution had been autoclaved before.

The transfection mixture (550 μl) was added to the cell suspension ($10^6$ cells) in the 15 ml tube, mixed well and the resulting transfection preparation kept in the incubator for one and a half hours at 37° C. After the step of incubation, 10 ml of culture medium were added and the cells separated by centrifugation at 1,000 rpm for 5 minutes. The cell precipitate was added to 10 ml of culture medium and the cell suspension kept on 9 cm plates in the incubator for 2 days. Six transfection experiments requiring $6 \times 10^6$ cells in total were carried out at the same time. In the transfection preparations the following vector DNAs, which have been described in more detail in Examples 1 and 2, were used:
1: pUC19
2: pL53In
3: pL53InCδ
4: pL53InCδrev
5: pL53In8
6: pL53In8rev

EXAMPLE 4

Production of RNA (description for one test tube)

The transfected cells were harvested as described in Example 3. By contrast, the cells from one plate were added to 5 ml of PBS after trypsin treatment and transferred to a 15 ml tube. The plate was washed once again with 5 ml of PBS and the cell suspension united in 15 ml tubes with the cells already harvested. The cell suspension was separated by centrifugation at 1,300 rpm for 10 minutes, the cell precipitate added to 1 ml of PBS at 4° C., transferred to an Eppendorf tube and washed twice with 1 ml of PBS each time (centrifugation in an Eppendorf centrifuge for 30 seconds at 2,000 rpm). After the last centrifugation the cell precipitate was broken up, added to 100 μl of RNA extraction buffer and mixed well (Vortex). The cells were lysed by adding 100 μl of RNA extraction buffer+1% NP40 for 5 minutes at 4° C.
RNA extraction buffer:
0.14M NaCl
1.5 mM $MgCl_2$
10 mM Tris HCl (pH 8.6)
1 mM dithiothreitol
20 mM vanadyl ribonucleoside complex.

The cell debris was separated by centrifugation in the Eppendorf centrifuge for 1 minute at 12,000 rpm and 4° C., the RNA containing supernatant transferred to a new Eppendorf tube, mixed with 200 μl of RK buffer and incubated for 30 minutes at 37° C.
RK buffer:
0.2M Tris HCl (pH 8.0)
25 mM EDTA (pH 8.0)
0.3M NaCl
2% SDS The Eppendorf tube was mixed with 400 μl of a phenol/chloroform (1:1) solution, shaken (Vortex) and centrifuged in the swinging bucket rotor of a Sorvall centrifuge for 5 minutes at 12,000 rpm. The aqueous phase was removed, transferred to a new Eppendorf tube and mixed with 400 μl of cold isopropanol (kept on ice for 30 minutes). The RNA was separated by centrifugation for 10 minutes at 13,000 rpm and 4° C., the RNA precipitate dried for a short time and washed with 70% ethanol. The 70% ethanol was removed completely, the RNA dried for a short time (for 10 minutes at room temperature) and then dissolved in 100 μl of $H_2O$ (for 10 minutes at 56° C.). The DNA still present in the RNA solution was removed by adding 100 μl of DNase mixture (for 15 minutes at 37° C.).
1 ml of DNase mixture contains:
100 μl of 10×DNase buffer (400 mM Tris HCl, pH 7.8; 100 mM NaCl; 60 mM $MgCl_2$)
1 μl of 1M dithiothreitol (DTT), 500 units of RNasin
100 μl (100 units) of DNase I (100 μg/ml), the remainder filled up with $H_2O$.

The DNase digestion was stopped after 15 minutes by adding 20 μl of stop solution (200 μl of $H_2O$; 24 μl of 10% SDS; 24 μl of 0.5M EDTA; pH 8). Then 300 μl of a phenol/chloroform (1:1) solution was added to the Eppendorf tube, the tube shaken (Vortex) and the phases separated by centrifugation for 5 minutes at 13,000 rpm. The aqueous (RNA containing) phase was transferred to a new Eppendorf tube and the RNA precipitated by adding 25 μl of 3M sodium acetate, pH 5.2, and 600 μl of ethanol (for 30 minutes at −20° C.; or overnight at −20° C.). After RNA precipitation, the Eppendorf tube was centrifuged for 10 minutes at 13,000 rpm and the RNA precipitate dissolved in 200 μl of TE, pH 7.2. The RNA solution was then mixed with 500 μl of ethanol and stored at −20° C.

EXAMPLE 5

Method for synthesizing cDNA and subsequently amplifying the cDNA by PCR.

The cDNA synthesis and PCR were carried out in the same buffer system ("Molecular Cloning", 1989, supra).

100 μl of a RNA/ethanol solution (1/7 of the RNA preparation) were mixed with 10 μl of 3M sodium acetate, pH 5.2, in an Eppendorf tube (shaking for 5 minutes at 4° C.), and the RNA separated by centrifugation for 10 minutes at 13,000 rpm. The RNA precipitate was washed once with 1 ml of 70% ethanol (centrifugation for 10 minutes at 13,000 rpm), dried for a short time and dissolved in 20 μl of $H_2O$ (kept on ice for 20 minutes). To the 20 μl of RNA solution were added:
4 μl of 10×PCR buffer
0.4 μl of 100 mM DTT
4 μl of 2 mM dNTPs
2 μl of 5′ insulin primer (8 μM)
2 μl of 3′ insulin primer (8 μM)
0.4 μl of RNasin (10 units/μl)
7 μl of $H_2O$
0.2 μl of reverse transcriptase (50 units/μl)
40 μl final volume.

10×PCR buffer:

100 mM Tris HCl, pH 8.3
500 mM KCl
15 mM MgCl$_2$
0.01% gelatin.

The 5' insulin primer had the following sequence (SEQ. ID No. 1):

5' GAG GGA TCC GCT TCC TGC CCC 3'.

The nucleotide of the primer at the 3' end was 179 bp away from the donor splice site of the 5' insulin exon. The 3' insulin primer had the following sequence (SEQ. ID No. 2):

5' CCC GGG CCA CCT CCA GTG CCC 3'.

The nucleotide at the 3' end of the primer was 71 bp away from the acceptor splice site of the 3' insulin exon. The cDNA synthesis was carried out for one hour at 42° C. In the cDNA synthesis, the reverse transcriptase of the avian myeloblastosis virus (AMV) was employed.

After the cDNA synthesis, 10 μl of 1×PCR buffer and 2.5 units of Taq polymerase were pipetted in the Eppendorf tube. The aqueous solution in the tube was layered with mineral oil and the Eppendorf tube placed in a heater (thermocycler) for PCR (25 to 30 cycles). Per cycle, the Eppendorf tube was kept at 94° C. for 1.4 minutes; at 60° C. for 1.4 minutes; and at 72° C. for 2.5 minutes. After PCR was completed, 10 μl (1/5) of reaction preparation were mixed with 2.5 μl of 5×dye buffer and placed on a 1% agarose gel to assay for potential PCR products. The methods described in Examples 4 and 5 for one transfection preparation each were also used for all 6 COS cells transfected with the various vectors (see Example 3). The analysis of the PCR products (cDNAs) obtained with RNA from those cells is shown in FIG. 6.

EXAMPLE 6

Cloning and sequencing of the PCR fragments obtained

20 μl of a positive PCR preparation (in which a DNA fragment containing a trapped exon was amplified) were digested with the restriction enzymes BamHI and SmaI and the thus cleaved DNA fragments cloned into plasmids pUC19 or pTZ19. The fragments cloned into pTZ19 were easy to sequence by using the 5' and 3' insulin primers in Sanger's technique. The sequence showed the exons to be correctly bound (spliced) to the insulin exons.

---

---

I claim:

1. A method for selectively cloning exons comprising the following steps:
  (a) cloning a genomic DNA fragment to be assayed for exons into a cloning site of a vector having the following features:
    (aa) said vector is a shuttle vector for prokaryotic and eukaryotic host cells which may contain selective marker genes,
    (ab) said vector contains a DNA fragment comprising the following elements arranged in the 5'-3' direction:
    a eukaryotic promoter,
    a 5' exon of a gene, and
    at least the 3'-terminal exon of a gene, said arrangement of elements permitting the synthesis of a functional transcript, with a cloning site being located in an intron following the 5' exon,
    thereby constructing a recombinant vector;
  (b) transfecting eukaryotic host cells with the recombinant vector;

(c) expressing the recombinant vector in the transfected host cells;
(d) isolating the total RNA from the host cells in (c);
(e) producing cDNA with the RNA indicated in (d), using a primer for the synthesis with reverse transcriptase, which primer is complementary to a region of an exon located downstream from the cloning site;
(f) carrying out a PCR reaction with the cDNA indicated in (e) and a primer pair, the first primer being complementary to a region of the exon located upstream from the cloning site and the second primer being complementary to a region of an exon located downstream from the cloning site;
(g) cloning in a vector the DNA fragment containing the additional exon(s) and obtained in the PCR reaction in (f).

2. A method for producing an exon library comprising the following steps:
(a) cloning genomic DNA fragments into a cloning site of vector molecules having the following features:
   (aa) said vector molecules are shuttle vectors for prokaryotic and eukaryotic host cells which may contain selective marker genes,
   (ab) said vector molecules contain a DNA fragment comprising the following elements arranged in the 5'-3' direction:
      a eukaryotic promoter,
      a 5' exon of a gene, and
      at least the 3'-terminal exon of a gene, said arrangement of elements permitting the synthesis of a functional transcript, with a cloning site being located in an intron following the 5' exon,
   thereby constructing recombinant vector molecules;
(b) transfecting eukaryotic host cells with the recombinant vector molecules;
(c) expressing the DNA fragment contained in the recombinant vector in the transfected host cells;
(d) isolating the total RNA from the host cells in (c);
(e) producing cDNA with the total RNA indicated in (d), using a primer for the synthesis with reverse transcriptase, which primer is complementary to a region of an exon located downstream from the cloning site;
(f) carrying out a PCR reaction with the cDNA indicated in (e) and a primer pair, the first primer being complementary to a region of the exon located upstream from the cloning site and the second primer being complementary to a region of an exon located downstream from the cloning site;
(g) cloning in vector molecules the DNA fragments containing the additional exon(s) and obtained in the PCR reaction in (f); and
(h) transforming or transfecting host cells for an exon library with the recombinant vectors obtained in (g).

3. The method as in claim 1 or 2, wherein said total RNA is poly(A) RNA.

4. The method as in claim 1 or 2 in which either primer used for the PCR reaction in (f) carries at its 5' end the recognition sequence of a desired restriction endonuclease.

5. The method as in claim 4 in which DNA fragments larger than the DNA fragment obtained only by the vector in the PCR reaction are isolated prior to cloning the DNA fragments of step (g) obtained by the PCR reaction.

6. The method as in claim 4 in which the recombinant vectors are propagated by cloning in a suitable host prior to steps (b) and/or (h).

7. The method as in claim 6, wherein said host is *E. coli*.

8. The method as in claim 4 in which the eukaryotic promoter is a strong promoter.

9. The method as in claim 8, wherein said promoter is LTR of RSV (Rous Sarcoma Virus).

10. The method as in claim 4 in which the exons integrated into the vector are derived from a rat insulin gene.

11. The method as in claim 4 in which the genomic DNA fragments are derived from a chromosomal region to be assayed.

12. The method as in claim 4 in which the genomic DNA fragments are derived from a genomic gene library.

13. A method for selectively cloning exons comprising the following steps:
(a) cloning a genomic DNA fragment to be assayed for exons into a cloning site of a vector having the following features:
   (aa) said vector is a shuttle vector for prokaryotic and eukaryotic host cells which may contain selective marker genes,
   (ab) said vector contains a DNA fragment comprising the following elements arranged in the 5'-3' direction:
      an LTR promoter of RSV (Rous Sarcoma Virus),
      a 5' exon of a rat insulin gene, and
      at least the 3'-terminal exon of a rat insulin gene, said arrangement of elements permitting the synthesis of a functional transcript, with a cloning site being located in an intron following the 5' exon,
   thereby constructing a recombinant vector;
(b) transfecting eukaryotic host cells with the recombinant vector;
(c) expressing the recombinant vector in the transfected host cells;
(d) isolating the poly(A) RNA from the host cells in (c);
(e) producing cDNA with the RNA indicated in (d), using a primer for the synthesis with reverse transcriptase, which primer is complementary to a region of an exon located downstream from the cloning site;
(f) carrying out a PCR reaction with the cDNA indicated in (e) and a primer pair, the first primer being complementary to a region of the exon located upstream from the cloning site and the second primer being complementary to a region of an exon located downstream from the cloning site;
(g) cloning in a vector the DNA fragment containing the additional exon(s) and obtained in the PCR reaction in (f).

14. A method for producing an exon library comprising the following steps:
(a) cloning genomic DNA fragments into a cloning site of vector molecules having the following features:
   (aa) said vector molecules are shuttle vectors for prokaryotic and eukaryotic host cells which may contain selective marker genes, (ab) said vector molecules contain a DNA fragment comprising the following elements arranged in the 5'-3' direction:
an LTR promoter of RSV (Rous Sarcoma Virus),
a 5' exon of a rat insulin gene, and
at least the 3'-terminal exon of a rat insulin gene, said arrangement of elements permitting the synthesis of a functional transcript, with a cloning site being located in an intron following the 5' exon,
thereby constructing recombinant vector molecules;
(b) transfecting eukaryotic host cells with the recombinant vector molecules;
(c) expressing the DNA fragment contained in the recombinant vector in the transfected host cells;
(d) isolating the poly(A) RNA from the host cells in (c);
(e) producing cDNA with the total RNA indicated in (d), using a primer for the synthesis with reverse transcriptase, which primer is complementary to a region of an exon located downstream from the cloning site;
(f) carrying out a PCR reaction with the cDNA indicated in (e) and a primer pair, the first primer being complementary to a region of the exon located upstream from the cloning site and the second primer being complementary to a region of an exon located downstream from the cloning site;
(g) cloning in vector molecules the DNA fragments containing the additional exon(s) and obtained in the PCR reaction in (f); and
(h) transforming or transfecting host cells for an exon library with the recombinant vectors obtained in (g).

15. The method as in claim 13 or 14 in which either primer used for the PCR reaction in (f) carries at its 5' end the recognition sequence of a desired restriction endonuclease.

16. The method as in claim 13 or 14 in which DNA fragments larger than the DNA fragment obtained only by the vector in the PCR reaction are isolated prior to cloning the DNA fragments of step (g) obtained by the PCR reaction.

17. An exon library obtainable by the method as in claim 2.

18. A vector having the following features:
(a) said vector is a shuttle vector for prokaryotic and eukaryotic host cells which may contain selective marker genes;
(b) said vector contains a DNA fragment comprising the following elements arranged in the 5'-3' direction:
a eukaryotic promoter,
a 5' exon of a gene, and
at least the 3'-terminal exon of a gene, said arrangement of elements permitting the synthesis of a functional transcript, with a polylinker being located in an intron following the 5' exon.

19. The vector as in claim 18 containing a genomic DNA fragment inserted into its polylinker.

20. The vector as in claim 18 or 19 in which the eukaryotic promoter is a strong promoter.

21. The vector as in claim 20, wherein said promoter is LTR of RSV (Rous Sarcoma Virus).

22. The vector as in claim 18 in which the exons integrated into the vector are derived from a rat insulin gene.

23. The vector as in claim 18 in which the genomic DNA fragment is derived from a chromosomal region to be assayed.

24. The vector as in claim 18 in which the genomic DNA fragments are derived from a genomic gene library.

25. A vector having the following features:
(a) said vector is a shuttle vector for prokaryotic and eukaryotic host cells which may contain selective marker genes;
(b) said vector contains a DNA fragment comprising the following elements arranged in the 5'-3' direction:
an LTR promoter of RSV (Rous Sarcoma Virus)
a 5' exon of a rat insulin gene, and
at least the 3'-terminal exon of a rat insulin gene,
a polylinker being located in an intron following the 5' exon,
a genomic DNA fragment inserted into said polylinker,
said arrangement of elements permitting the synthesis of a functional transcript.

26. A host organism transfected or transformed with a vector as in claim 18.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

GAGGGATCCG CTTCCTGCCC C      21

( 2 ) INFORMATION FOR SEQ ID NO:2:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:2:

CCCGGGCCAC CTCCAGTGCC C      21